United States Patent
Yin et al.

(10) Patent No.: US 12,409,093 B2
(45) Date of Patent: Sep. 9, 2025

(54) FINGER JOINT REHABILITATION TRAINING DEVICE

(71) Applicant: Shanghai Siyi Intelligent Technology Co., Ltd., Shanghai (CN)

(72) Inventors: Ganggang Yin, Shanghai (CN); Wudong Wang, Shanghai (CN); Zhongzhe Chen, Shanghai (CN)

(73) Assignee: Shanghai Siyi Intelligent Technology Co.,Ltd., Shanghai (CN)

( * ) Notice: Subject to any disclaimer, the term of this patent is extended or adjusted under 35 U.S.C. 154(b) by 733 days.

(21) Appl. No.: 17/795,373

(22) PCT Filed: Dec. 10, 2020

(86) PCT No.: PCT/CN2020/135244
§ 371 (c)(1),
(2) Date: Jul. 26, 2022

(87) PCT Pub. No.: WO2021/115376
PCT Pub. Date: Jun. 17, 2021

(65) Prior Publication Data
US 2023/0108327 A1 Apr. 6, 2023

(30) Foreign Application Priority Data

Dec. 11, 2019 (CN) .......................... 201911263347.4
Dec. 10, 2020 (CN) .......................... 202011431505.5

(51) Int. Cl.
*A61H 1/02* (2006.01)
*A61B 5/00* (2006.01)
*A61B 5/11* (2006.01)

(52) U.S. Cl.
CPC .......... *A61H 1/0288* (2013.01); *A61B 5/1125* (2013.01); *A61B 5/4836* (2013.01);
(Continued)

(58) Field of Classification Search
CPC .......... A61H 1/0288; A61H 2201/1238; A61H 2201/1638; A61H 2201/165;
(Continued)

(56) References Cited

U.S. PATENT DOCUMENTS

| 2013/0072836 | A1 | 3/2013 | Patrick et al. | |
|---|---|---|---|---|
| 2016/0162022 | A1* | 6/2016 | Seth | G06F 3/017 345/156 |
| 2021/0081042 | A1* | 3/2021 | Baier | G06F 3/014 |

FOREIGN PATENT DOCUMENTS

| CN | 2725994 Y | 9/2005 |
|---|---|---|
| CN | 104207782 A | 12/2014 |

(Continued)

OTHER PUBLICATIONS

International Search Report, China National Intellectual Property Administration, Application No. PCT/CN2020/135244, mailed Mar. 9, 2021, 6 pages.

*Primary Examiner* — Kendra D Carter
*Assistant Examiner* — Arielle Wolff
(74) *Attorney, Agent, or Firm* — ZIEGLER IP LAW GROUP, LLC.

(57) ABSTRACT

The present disclosure provides a finger joint rehabilitation training device, which includes a control member, a data acquisition member, a gas circuit system, and a wearable training member. The wearable training member is provided with a pneumatic component that can expand and contract. The data acquisition member is configured for acquiring hand motion information of a first hand and transmitting the hand motion information to the control member. The hand motion information includes hand pressing information. The control member controls the gas circuit system to inflate the pneumatic component or to draw air from the pneumatic component according to the hand motion information, to make the wearable training member change between a
(Continued)

flexion condition and a stretching condition, so as to realize a hand mirror training of a second hand. The hand pressing information is simple and convenient to acquire, which is convenient for the first hand to realize the flexion condition and the stretching condition, and the condition of the second hand is adjusted through the condition of the first hand, so that the wearable training member can be better adjusted, different hand training intensity requirements are met, and a better training effect is achieved.

20 Claims, 6 Drawing Sheets

(52) U.S. Cl.
CPC .... *A61B 5/6806* (2013.01); *A61B 2562/0247* (2013.01); *A61H 2201/1238* (2013.01); *A61H 2201/1638* (2013.01); *A61H 2201/165* (2013.01)

(58) Field of Classification Search
CPC .... A61H 2201/0107; A61H 2201/1409; A61H 2201/1261; A61H 2201/1635; A61H 2201/5023; A61H 2201/5043; A61H 2201/5056; A61H 2201/5061; A61H 2201/5071; A61H 2201/5074; A61H 2201/5087; A61H 2201/5092; A61H 2201/5097; A61H 2230/625; A61H 1/0285; A61H 2201/5035; A61H 2201/5058; A61H 9/0078; A61H 2201/501; A61H 2205/067; A61B 5/1125; A61B 5/4836; A61B 5/6806; A61B 2562/0247; A61B 5/002; A61B 5/1114; A61B 5/4848; A61B 2505/09; A61B 2562/0233; A61B 2562/12

See application file for complete search history.

(56) References Cited

FOREIGN PATENT DOCUMENTS

| | | | |
|---|---|---|---|
| CN | 106037648 | A | 10/2016 |
| CN | 208426594 | U | 1/2019 |
| CN | 109875850 | A | 6/2019 |
| CN | 109999429 | A | 7/2019 |
| CN | 110141456 | A | 8/2019 |
| CN | 110353940 | A | 10/2019 |
| CN | 110801372 | A | 2/2020 |
| CN | 211584109 | U | 9/2020 |
| CN | 109044740 | A | 2/2021 |
| CN | 112370310 | A | 2/2021 |
| CN | 112370311 | A | 2/2021 |
| CN | 112494274 | A | 3/2021 |
| CN | 112773666 | A | 5/2021 |
| KR | 20180072264 | A | 6/2018 |
| KR | 20180134083 | A | 12/2018 |

\* cited by examiner

FINGER JOINT REHABILITATION TRAINING DEVICE

This application is based upon and claims priority to Chinese Patent Application No. 201911263347.4, filed on Dec. 11, 2019 and No. 202011431505.5, filed on Dec. 10, 2020, the entire contents of which are incorporated herein by reference.

TECHNICAL FIELD

The present disclosure relates to the technical field of finger rehabilitation training, in particular to a finger joint rehabilitation training device.

BACKGROUND ART

With the accelerating process of population aging and the increasing incidence of stroke year by year, the number of stroke in China is increasing. The number of patients with post-stroke dysfunction, especially hand dysfunction, is increasing year by year, and hand dysfunction has seriously affected the quality of life of the patients.

With the development of science and technology, there are already some devices for finger joint rehabilitation training, but these hand joint rehabilitation training devices can only carry out passive rehabilitation training, which requires preset training time and training intensity. Patients receive passive rehabilitation training according to preset time and action, it can't be adjusted and controlled according to the real-time situation of users. At the same time, the patients can't control the training process and training plan independently, and the mode is relatively simple. Moreover, it is easy to have hand overload training injury or insufficient hand rehabilitation training intensity in the passive training process.

The patent published No. KR10-2018-0072264A discloses a hand rehabilitation training system and a training method, the patent published No. KR10-2018-0134083A discloses a ball type hand joint rehabilitation apparatus and a rehabilitation system including the same, and the patent published No. CN208426594U discloses a gripper for resisting hand scar contracture. All the three inventions adopt the method of pressing for hand training, and adopt a method of air bag for pressing, but the air bag is large in volume, so when it is gripped in the hand for pressing, the fingers can only bend slightly, and it is difficult to make a fist, which will lead to insufficient hand training intensity and poor training effect. Moreover, the three inventions can only carry out autonomous hand training, and for people whose hands are seriously injured and whose hands have temporarily lost all their motor ability and need rehabilitation training assisted by other equipment to resume hand movement, the devices of the three inventions cannot be used for active first clenching training.

The patent publication No. CN110141456A discloses a soft hand rehabilitation gloves combined with diverse rehabilitation training modes, which includes training gloves, soft exoskeleton fingers and a pneumatic control system. The device can feed or unload gas to/from the soft finger body through a gas circuit system, so as to drive the finger to realize flexion or stretching action. However, the device can only provide passive rehabilitation training or impedance training based on the pressure control of the gas circuit system. The rehabilitation training mode is relatively simple, and the passive rehabilitation can only be carried out according to the set procedures, and the time, movement and intensity of rehabilitation training cannot be adjusted independently. It is easy to cause hand injury due to high rehabilitation intensity, or the rehabilitation training effect cannot be achieved due to low intensity. The patients' sense of participation is low and the rehabilitation effect is poor.

Therefore, it is necessary to provide a novel finger joint rehabilitation training device to solve the above problems in the prior art.

SUMMARY

The present disclosure aims at providing a finger joint rehabilitation training device, which controls and achieves hand mirror training of a second hand by acquiring hand pressing information of a first hand.

To achieve the above purpose, the finger joint rehabilitation training device of the present disclosure includes a control member, a data acquisition member connected to the control member, a gas circuit system connected to the control member and a wearable training member connected to the gas circuit system, wherein the wearable training member is provided with a pneumatic component that can expand and contract, and the data acquisition member is configured for acquiring hand motion information of a first hand and transmitting the hand motion information to the control member, the hand motion information includes hand pressing information; the control member is configured for controlling the gas circuit system to supply air to the pneumatic component or to draw air from the pneumatic component according to the hand motion information, so that the wearable training member perfoms a transition between a flexed state and an extended state, so as to realize a hand mirror training of a second hand.

The finger joint rehabilitation training device of the present disclosure has the beneficial effect that: the acquisition of the hand pressing information can be realized by a way of pressing, the hand motion information is simple and convenient, it is convenient for the first hand to realize the flexed state and the extended state, the data acquisition member acquires the hand motion information of the first hand and transmits the hand motion information to the control member, the control member controls the gas circuit system to supply air to the pneumatic component or to draw air from the pneumatic component according to the hand motion information, the wearable training member is changed between the flexed state and the extended state, to realize the hand mirror training of the second hand, so that a condition of the second hand can be adjusted by a condition of the first hand, that is, time, movement and intensity of the rehabilitation training for the second hand can be autonomously adjusted through collecting the hand motion information of the first hand, so that the wearable training member can be better adjusted to meet the training requirements of the second hand.

Preferably, the finger joint rehabilitation training device further includes a wearable data member, the wearable data member is in a shape of a glove, and the data acquisition member is disposed at a palm corresponding location of the wearable data member. The present disclosure has the beneficial effect that the data acquisition member is disposed on the wearable data member, which can effectively prevent the data acquisition member from falling off the hand of the user, is convenient for the user to use the data acquisition member, and is especially suitable for people with insensitive hands; and the data acquisition member is disposed at the palm corresponding location of the wearable data member, which is convenient for the finger pulp or fingertip of each finger to be pressed to the data acquisition member when the user clenches a fist.

Preferably, the palm corresponding location is provided with an accommodating part, the data acquisition member is disposed in the accommodating part, and the data acquisition member is detachably connected to the accommodating part. The present disclosure has the beneficial effect that the data acquisition member is easy to disassemble and the wearable data member is easy to clean.

Further preferably, the accommodating part is of a long and narrow structure, and the data acquisition member is long and narrow and fits with the accommodating part. The present disclosure has the beneficial effect that the long and narrow accommodating part is convenient for loading the data acquisition member, and the data acquisition member is of a long and narrow structure, which ensures that the finger pulp or fingertip of each finger can be pressed to the data acquisition member when the user clenches a fist, thereby avoiding the situation that the data acquisition member cannot be used because the finger pulp or fingertip of some fingers of the user cannot be pressed to the data acquisition member under special circumstances (such as finger injury, or holding something, etc.) or some special people (people with unsound five fingers).

Preferably, the data acquisition member is fixed to the palm corresponding location by any one of pasting, hook and loop, magnetic attraction, sewing and buckling. The present disclosure has the beneficial effect that when a user clenches a fist, the finger pulp or the fingertip of each finger can be pressed to the data acquisition member, the fixing mode is simple and convenient, and the cost is low.

Preferably, a minimum linear distance between a first axis of the data acquisition member and a palm root line of the palm is not less than 1 cm, and a minimum linear distance between the first axis of the data acquisition member and a metacarpophalangeal joint line of the palm is not less than 0.5 cm. The present disclosure has the beneficial effect that if the data acquisition member is set beyond this range, when the user clenches a fist, the finger pulp or fingertip cannot be pressed to the data acquisition member, a position of the data acquisition member is matched with a position where the finger pulp or fingertip is pressed on the palm when the user clenches a fist, so that the finger pulp or fingertip can be pressed to the data acquisition member when the user clenches a fist, and the effective hand motion information of the first hand is conveniently acquired.

Preferably, a length of the first axis of the data acquisition member is 10% to 100% of an axial length of the palm. The present disclosure has the beneficial effect to ensure that the finger pulp or fingertip can be pressed to the data acquisition member when the user clenches a fist, it is convenient to acquire effective hand motion information of the first hand, a size of the data acquisition member is set according to a size of the palm corresponding location of the wearable data member, and the size of the data acquisition member being relatively small can save the material input cost of the data acquisition member, and is suitable for users with sound and flexible hand fingers, and the size of the data acquisition member being relatively large can ensure that the finger pulp or fingertip of either finger can be pressed to the data acquisition member when the user clenches a fist, and is suitable for users with inflexible hand fingers.

Preferably, an included angle between the first axis of the data acquisition member and an inner palm edge line of the palm is greater than 0° and less than 180°. The present disclosure has the beneficial effect that because an included angle between a contact point between the finger pulp or fingertip and the palm and the inner palm edge line is different when different users clench fists, an angle of the data acquisition member in the palm corresponding location is set according to an actual contact position of the finger pulp or the fingertip and the palm when the user clenches a fist, so that the finger pulp or the fingertip can be easily pressed to the data acquisition member when the user clenches a fist.

Preferably, the data acquisition member includes a pressing unit including m conductive sheets, where m is a natural number greater than or equal to 1. The present disclosure has the beneficial effect that the hand motion information of the user is conveniently acquired by means of an electrical signal; and the pressing unit includes m conductive sheets, which ensures contact sensitivity, the data acquisition member in a form of conductive sheets features better support and stability.

Further preferably, the data acquisition member further includes a housing, the pressing unit is disposed in the housing, a pressing member is disposed on an outer side of the housing, the pressing member is made of an elastic material, and the pressing member is disposed in parallel with the conductive sheets. The present disclosure has the beneficial effect that the pressing member is made of the elastic material, which is convenient for pressing the pressing unit through the pressing member, and when the conductive sheets are disposed in parallel with the pressing member, so that labor is saved during pressing.

Further preferably, the control member includes a signal detection unit, and the signal detection unit is electrically connected to the pressing unit. The present disclosure has the beneficial effect that it is convenient to detect whether the pressing unit is pressed or not.

Further preferably, the data acquisition member includes a housing and a pressing unit disposed in the housing, the pressing unit includes at least one pressure sensitive device, the outer side of the housing is provided with a pressing member, the pressing member is made of an elastic material, the control member includes a signal detection unit, the signal detection unit is electrically connected to the pressing unit. The present disclosure has the beneficial effect that at least one pressure sensitive device ensures the sensitivity of the contact and avoids failure to press the pressure sensitive device when pressed.

Preferably, the data acquisition member includes a pressure sensitive element, the pressure sensitive element includes an elastic housing and a conductive adhesive layer, wherein the conductive adhesive layer is composed of a conductive adhesive and a copper wire embedded in the conductive adhesive, the conductive adhesive layer includes a first conductive adhesive layer and a second conductive adhesive layer, the first conductive adhesive layer and the second conductive adhesive layer are not in contact with each other and are respectively disposed on opposite inner side walls of the elastic housing. The present disclosure has the beneficial effect that the data acquisition member is in a form of a pressure sensitive element, has good softness, is easier to press and acquire hand pressing information, and has a simple structure and ingenious design; the first conductive adhesive layer and the second conductive adhesive layer are not in contact with each other and are respectively disposed on the opposite inner side walls of the elastic housing, and when a finger presses the pressure sensitive element, the first conductive adhesive layer and the second conductive adhesive layer are in contact with each other to generate an electrical signal, thereby acquiring the hand pressing information.

Further preferably, the control member includes a signal detection unit, and the signal detection unit is electrically connected to the pressure sensitive element via the copper wire. The present disclosure has the beneficial effect that it is easy to detect the electrical signal generated by the first conductive adhesive layer and the second conductive adhesive layer in contact with each other.

Further preferably, the data acquisition member also includes a conductive part, the conductive part is disposed at one end of the elastic housing, and upper and lower end faces of the conductive part are respectively in contact with the first conductive adhesive layer and the second conductive adhesive layer, the control member includes a signal detection unit, and the signal detection unit is electrically connected to the pressure sensitive element via the conductive part. The present disclosure has the beneficial effect that the upper and lower end faces of the conductive part are respectively in contact with the first conductive adhesive layer and the second conductive adhesive layer, which not only increases the supporting strength at a head end of the pressure sensitive element, but also makes the electrical signal acquisition more sensitive.

Preferably, the hand motion information further includes hand light sensing information. The present disclosure has the beneficial effect that the hand light sensing information is easier to acquire without pressing, the hand light sensing information can be obtained as long as the finger flexes to block the light path, thereby driving the second hand to perform hand mirror training, the user's operation can be responded more easily and quickly, the present disclosure is suitable for people with insensitive hands, especially for people with incomplete or stiff fingers, so that a user can acquire the hand motion information by pressing or shielding the data acquisition member, and can effectively prevent the situation that the hand motion information cannot be acquired due to the inability of the user to press the data acquisition member.

Further preferably, the data acquisition member includes at least one light sensing unit, and the control member includes a signal detection unit, and the signal detection unit is electrically connected to the light sensing unit. The present disclosure has the beneficial effect that the data acquisition member includes at least one light sensing unit, which ensures the sensitivity of light sensing information acquisition; and the control member includes a signal detection unit, which is electrically connected to the light sensing unit to facilitate the acquisition of the hand light sensing information.

Further preferably, an included angle between a path direction of light emitted by the light sensing unit and a direction of a finger member where the finger member is straightened is 0° to 180°. The present disclosure has the beneficial effect that when the fingers bend or make a fist, the path of the light emitted by the light sensing unit is blocked, so as to trigger the light sensing unit to respond and convert a light signal into an electrical signal, thereby acquiring the hand light sensing information.

Preferably, the data acquisition member is any one of a spherical structure, an ellipsoidal structure and a polyhedral structure. The present disclosure has the beneficial effect of various forms and beautiful appearance.

Preferably, a thickness of the data acquisition member is 0.1 cm to 2 cm. The present disclosure has the beneficial effect that the thickness of the data acquisition member is small so that the training intensity can be adjusted; on the one hand, the data acquisition member is placed in the palm of the hand, and the user can press the finger pulp or fingertip of each finger to the palm of the hand by clenching the fist, and a flexion angle of the finger joints is larger when clenching the fist, which increases the training intensity of the finger joints and can fully train the finger joint; on the other hand, the user can press the data acquisition member through cooperation of the thumb and other fingers, so that the flexion angle of the finger joints is small, the training intensity is small, to ensure an appropriate training intensity, and avoid the injury to the hand due to the training intensity exceeding the hand load.

Preferably, at least one surface of the housing of the data acquisition member is a concave-convex surface. The present disclosure has the beneficial effect that convex points, concave-convex stripes, concave-convex patterns are formed on at least one surface of the housing of the data acquisition member to form a concave-convex surface, the concave-convex surface is easy to process and can provide a good anti-skid effect.

Preferably, the finger joint rehabilitation training device further includes a peripheral end, and the peripheral end includes a mobile display member, a mobile key member, a first data interaction module and a mobile control member, and the mobile display member, the mobile key member and the first data interaction module are all disposed on the mobile control member. The present disclosure has the beneficial effect that the remote control of the finger joint rehabilitation training device is facilitated through the peripheral end.

Further preferably, the control member is provided with a second data interaction module for transmitting data with the first data interaction module. The present disclosure has the beneficial effect that the data transmission with an external end is convenient.

Preferably, the gas circuit system includes a first pump, a second pump, a first valve and a second valve, the first pump, the second pump and the second valve are connected through a first three-way pipe, the first pump, the second pump and the first valve are connected through a second three-way pipe, and the first valve, the second valve and the wearable training member are connected through a third three-way pipe. The present disclosure has the beneficial effect that the first pump and the second pump are two pumps in total, in the case of the same air flow, the volume of the two pumps is smaller than the volume of one pump, and the noise of the two pumps is smaller than that of one pump; and there are two pumps in total, i.e., the first pump and the second pump, and two valves in total, i.e., the first valve and the second valve, so that any one of the pumps can work alone or two pumps can work at the same time, which is convenient for switching the training intensity of strong and weak gears.

Preferably, the finger joint rehabilitation training device further includes a device housing and a battery, wherein the battery, the gas circuit system and the control member are sequentially disposed in the device housing from bottom to top, and the gas circuit system is connected to the battery through the control member.

Further preferably, the battery, the gas circuit system, the control member and the device housing are provided with damping cotton between each other. The present disclosure has the beneficial effect of preventing collision among the battery, the gas circuit system, the control member and the device housing due to vibration.

Further preferably, an upper side of the device housing is provided with a key member, and the key member is connected to the control member.

DETAILED DESCRIPTION

In order to make objectives, technical solutions, and advantages of the disclosure clearer, the technical solutions in the present disclosure are described clearly and completely in the following with reference to accompanying drawings in the embodiments of the disclosure. Apparently, the described embodiments are only part rather than all of the embodiments of the disclosure. Based on the embodiments of the present disclosure, all the other embodiments obtained by those of ordinary skill in the art without inventive effort are within the scope of the present disclosure. Unless otherwise mentioned, all technical and scientific terms used herein have the same meaning as commonly understood by one of ordinary skill in the art to which the present disclosure belongs. The term "including" and the like as used herein means that the elements or articles appearing before the term encompass the enumerated elements or articles appearing after the term and their equivalents, without excluding other elements or articles.

Figure 1:
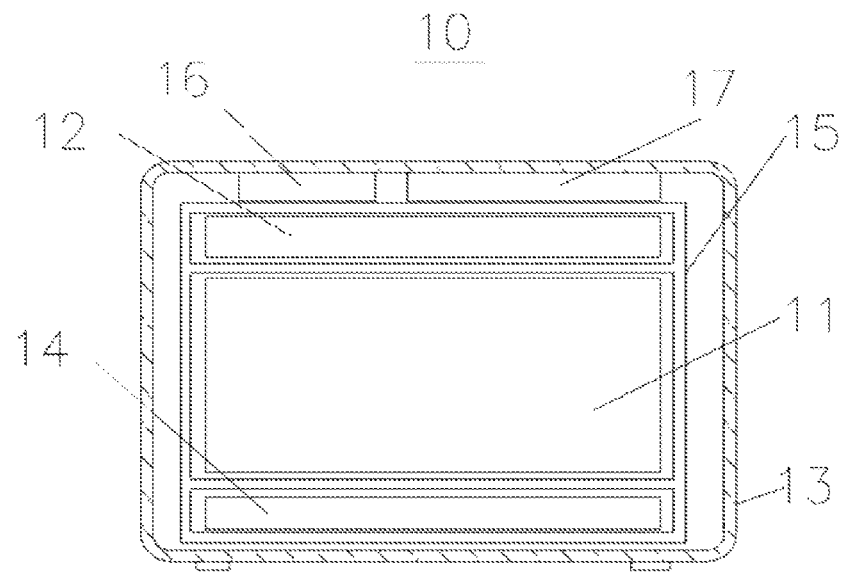
FIG. 1 is a cross-sectional structural diagram of a finger joint rehabilitation training device of the present disclosure.

FIG. 1 is a cross-sectional structural diagram of a finger joint rehabilitation training device of the present disclosure.

In view of the problems existing in the prior art, the embodiments of the present disclosure provide a finger joint rehabilitation training device, as shown in FIG. 1, a finger joint rehabilitation training device 10 includes a control member 12, a data acquisition member (not shown) connected to the control member 12, a gas circuit system 11 connected to the control member 12 and a wearable training member (not shown) connected to the gas circuit system 11. The wearable training member is provided with a pneumatic component that can expand and contract (not shown). The data acquisition member is configured for acquiring hand motion information of a first hand and transmitting the hand motion information to the control member 12. The hand motion information includes hand pressing information. The control member 12 is configured for controlling the gas circuit system 11 to inflate the pneumatic component or to draw air from the pneumatic component according to the hand motion information, to make the wearable training member change between a flexion condition and a stretching condition, so as to realize a hand mirror training of a second hand. The acquisition of the hand pressing information can be realized by a way of clenching a fist, the hand motion information is simple and convenient, it is convenient for the first hand to realize the flexion condition and stretching condition, so that a condition of the second hand can be adjusted by a condition of the first hand, that is, rehabilitation training time, movement and intensity of the second hand can be autonomously adjusted through the acquisition of the hand motion information of the first hand, so that the wearable training member can be better adjusted to meet the training requirements of the second hand. The first hand and the second hand are left or right hand of a user, and the mirror training means that the second hand moves with reference to the movement of the first hand.

In some embodiments of the present disclosure, referring to FIG. 1, the finger joint rehabilitation training device 10 further includes a device housing 13 and a battery 14. The battery 14, the gas circuit system 11 and the control member 12 are sequentially disposed in the device housing 13 from bottom to top, and the battery 14, the gas circuit system 11, the control member 12 and the device housing 13 are provided with damping cotton 15 between each other. The battery 14 is connected to the control member 12 and supplies power to the gas circuit system 11 through the control member 12.

In some embodiments of the present disclosure, one side of the device housing is provided with a charging port, the charging port is connected to the battery, and the charging port is used for connecting with an external power supply to realize charging the battery.

In some embodiments of the present disclosure, referring to FIG. 1, a key member 16 is provided on an upper side of the device housing 13, and the key member 16 is connected to the control member 12. The key member 16 is used for sending an operation instruction to the control member 12. Specifically, the key member 16 includes a key for starting the finger joint rehabilitation training device, a key for closing the finger joint rehabilitation training device, a key for performing hand mirror training, a key for performing autonomous hand training, and training mode keys. In certain embodiments of the present disclosure, the training mode includes a multi-finger training mode and a single-finger training mode, the multi-finger training mode includes a five-finger training mode, a two-finger training mode, a three-finger training mode, a four-finger training mode, etc. The single-finger training refers to training a single finger, and the selection and control of the training mode is the common knowledge in the art, which will not be repeated here.

In some embodiments of the present disclosure, the control member 12 is also connected with an information feedback member 17, and the control member 12 is used for feeding back the operation information of the first hand through the information feedback member 17 according to the hand motion information, so that the first hand can perform autonomous hand training according to the operation information.

In some specific embodiments of the present disclosure, referring to FIG. 1, the information feedback member 17 is a display screen, and the display screen is disposed on the upper side of the device housing 13. The key member 16 is used for transmitting an operation instruction to the control member 12. The display screen is used for displaying the operation information fed back by the control member 12. The display screen is also used for displaying a current working state, working mode and time, etc.

In some embodiments of the present disclosure, the autonomous hand training includes hand action games and the like. Specifically, game software is stored in the control member, and when the user's hand is flexed, the data acquisition member acquires the hand motion information of hand flexion to control a left movement of a character in the game software, and when the user stretches the hand, the data acquisition member acquires the hand motion information of the hand stretching to control a right movement of the character in the game software. Game images are displayed by a display device. Through the way of game, users can train their hands independently. Driven by the fun of the game, users are happy to train independently. The left movement of the character in the game software and the right movement of the character in the game software are the operation information fed back by the control member.

In some embodiments of the present disclosure, the finger joint rehabilitation training device further includes a terminal equipment. The terminal equipment includes a communication module. The communication module is communicated with the control member. Image(s) and/or sound are pre-stored in the terminal equipment. The data acquisition member acquires the hand motion information of the first hand and transmits the hand motion information to the control member. The control member communicates with the terminal equipment through the communication module, and controls image movement and/or sound changes in the terminal equipment. The first hand can autonomously adjust the acquisition of hand motion information of the first hand according to the real-time situation of the user to carry out autonomous hand training. The training intensity can be adjusted autonomously, and the autonomous training is more flexible, and is more appropriate to the actual situation of users, which improves the training effect, and feeding back hand motion information of the first hand by driving image motion and/or sound changes enables the user to get the training feedback result in real time, results in intuitive rehabilitation training effect of the training, and can accurately reflect a completion of patient's hand motions, and driven by the fun of the game, users are willing to carry out independent training, which improves the enthusiasm of the user for autonomous training and has high training compliance.

In some preferred embodiments of the present disclosure, the control member controls the gas circuit system to inflate the pneumatic component or to draw air from the pneumatic component according to the hand motion information, the wearable training member is changed between a flexion condition and a stretching condition, to realize the hand mirror training of the second hand. At the same time, the control member also communicates with the terminal equipment through the communication module, and controls image movement and/or sound changes in the terminal equipment, such that the hand motion information of the first hand is fed back by driving image movement and/or sound change, and the user can get the training feedback result in real time, the rehabilitation training effect of the training is intuitive, and a completion of patient's hand motions can be accurately reflected. Driven by the fun of the game, the user is willing to carry out autonomous training, which improves the enthusiasm of the user for autonomous training and has high training compliance.

In some embodiments of the present disclosure, an image is stored in the terminal equipment. When the user flexes the hand to press the pressing unit, the data acquisition member acquires the hand pressing information of the first hand of the hand flexing to control the image in the terminal equipment (such as a character, an animal or an automobile, etc.) to move left; and when the palm of the user is extended, the data acquisition member acquires the hand pressing information of the first hand where the palm is extended, so as to control the image (such as a character, an animal, an automobile, etc.) in the terminal equipment to move right. The image is displayed by a display device. Through the game-like way, users can train their hands independently. Driven by the fun of the game, users are happy to train independently.

In some preferred embodiments of the present disclosure, the information feedback member further includes a scoring unit, a first scoring standard is pre-stored in the scoring unit, and the control member is used for calling the first scoring standard and movement information of the information feedback member to perform comparative analysis to score the hand motion information, so as to stimulate the training interest of the user, thereby enabling the user to be willing to carry out autonomous training and having high training compliance. In some embodiments of the present disclosure, the first scoring standard scores according to a percentile system, and the scoring unit scores based on the pre-stored scores when the information feedback member feeds back the movement information of the user. The scoring method is a known technique in the game field. Specifically, the first scoring standard presets a standard movement and its score based on each movement in the game, the control member calls the first scoring standard, compares the standard movement with the movement information of the information feedback member, finds out a coincidence movement of the movement information of the information feedback member and the standard movement and the corresponding score value, and gives the score to the hand motion information, which will not be repeated here. In certain other preferred embodiments of the present disclosure, the first scoring standard is graded according to a hierarchy, which in some embodiments includes ten grades.

In some embodiments of the present disclosure, sound (such as music, etc.) is stored in the terminal equipment. When the user flexes the hand to press the pressing unit, the data acquisition member acquires the hand pressing information of the first hand of the hand flexing to control the sound in the terminal equipment to become louder (or switch to the next song); and when the hand of the user is extended, the data acquisition member acquires the hand pressing information of the first hand where the hand is extended, so as to control the sound in the terminal equipment to be reduced (or switch to the previous song). The sound is played by a music player. Through the game-like way, users can train their hands independently. Driven by the fun of the game, users are happy to train independently.

In some embodiments of the present disclosure, the hand mirror training and the autonomous hand training can be selected by the control member.

In some embodiments of the present disclosure, for users who are unable to extend and flex their hands by themselves due to severe hand injuries, a wearable training member can be worn on the hand and a gas circuit system connected to the wearable training member can be provided to assist in the autonomous training.

Figure 2:
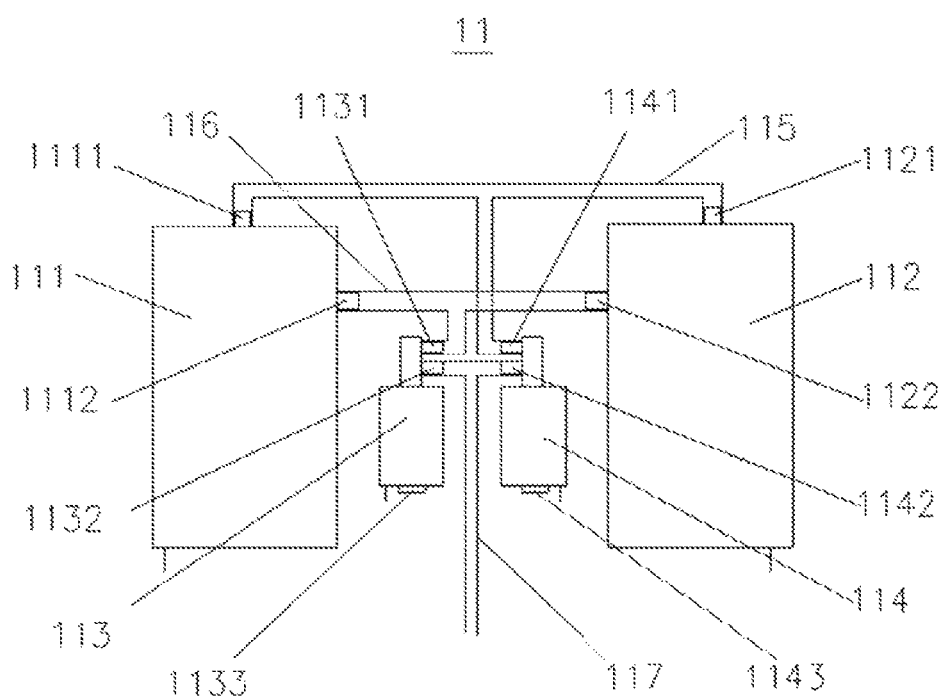
FIG. 2 is a structural diagram of a gas circuit system of the present disclosure.

FIG. 2 is a structural diagram of a gas circuit system of the present disclosure. In some embodiments of the present disclosure, referring to FIG. 2, the gas circuit system 11 includes a first pump 111, a second pump 112, a first valve 113 and a second valve 114. Specifically, when the finger joint rehabilitation training device 10 is placed on a horizontal plane, the first pump 111, the second pump 112, the first valve 113 and the second valve 114 are located in a same plane parallel to a horizontal plane. The first valve 113 and the second valve 114 are located between the first pump 111 and the second pump 112, which can reduce a layout difficulty of a connecting pipeline between the first pump 111, the second pump 112, the first valve 113 and the second valve 114, and can reduce an overall volume of the finger joint rehabilitation training device. A line of centers of the first pump 111 and the second pump 112 is perpendicular to length directions of the first pump 111 and the second pump 112. A line of centers of the first valve 113 and the second valve 114 is perpendicular to length directions of the first valve 113 and the second valve 114, so that a flat layout of two pumps and two valves can be realized, and the overall volume of the finger joint rehabilitation training device can be further reduced. The length directions of the first pump 111 and the second pump 112 are parallel to the length directions of the first valve 113 and the second valve 114, so that the first pump 111, the second pump 112, the first valve 113 and the second valve 114 are more concentrated without being dispersed, and an overall length of the finger joint rehabilitation training device 10 is reduced. On one hand, the first pump and the second pump are two pumps in total, in the case of the same air flow, the volume of the two pumps is smaller than the volume of one pump, and the noise of the two pumps is smaller than that of one pump. On the other hand, there are two pumps and two valves, so that any one of the pumps can work alone or two pumps can work at the same time, which is convenient for switching the training intensity of strong and weak gears.

In some embodiments of the present disclosure, referring to FIG. 2, the first pump 111, the second pump 112 and the second valve 114 are connected by a first three-way pipe 115, the first pump 111, the second pump 112 and the first valve 113 are connected by a second three-way pipe 116, and the first valve 113, the second valve 114 and the wearable training member (not shown) are connected by a third three-way pipe 117.

In some embodiments of the present disclosure, referring to FIG. 2, the first pump 111 is provided with a first positive pressure port 1111 and a first negative pressure port 1112, the second pump 112 is provided with a second positive pressure port 1121 and a second negative pressure port 1122, the first valve 113 is provided with a first permanent opening 1131, a first regulating port 1132 and a first external interface 1133, and the second valve 114 is provided with a second permanent opening 1141, a second regulating port 1142 and a second external interface 1143. A first connection port (not shown) of the first three-way pipe 115 is connected to the first positive pressure port 1111, a second connection port (not shown) of the first three-way pipe 115 is connected to the second positive pressure port 1121, and a third connection port (not shown) of the first three-way pipe 115 is connected to the second permanent opening 1141, thereby ensuring the air flow at the second permanent opening 1141. A first connection port (not shown) of the second three-way 116 is connected to the first negative pressure port 1112, a second connection port (not shown) of the second three-way pipe 116 is connected to the second negative pressure port 1122, and a third connection port (not shown) of the second three-way pipe 116 is connected to the first permanent opening 1131, thereby ensuring the air flow at the first permanent opening 1131. A first connection port (not shown) of the third three-way pipe 117 is connected to the first regulating port 1132, a second connection port (not shown) of the third three-way pipe 117 is connected to the second regulating port 1142, and a third connection port (not shown) of the third three-way pipe 117 is connected to the wearable training member (not shown), thereby ensuring the air flow into or out of the wearable training member.

In some embodiments of the present disclosure, the first pump, the second pump, the first valve, and the second valve are all electrically connected to the control member, which controls receiving the operation instruction to power on or off the first pump, the second pump, the first valve, or the second valve. When the first pump is powered on, the second pump can be powered on or off. When the first pump is powered off, the second pump can be powered on or off.

In some embodiments of the present disclosure, both the first valve and the second valve are electromagnetic valves. When the first valve is powered off, the first permanent opening is communicated with the first external interface, and the first regulating port is closed. When the first valve is powered on, the first permanent opening is communicated with the first regulating port, and the first external interface is closed. When the second valve is powered off, the second permanent opening is communicated with the second external interface, and the second regulating port is closed. When the second valve is powered on, the second permanent opening is communicated with the second regulating port, and the second external interface is closed.

Figure 3:
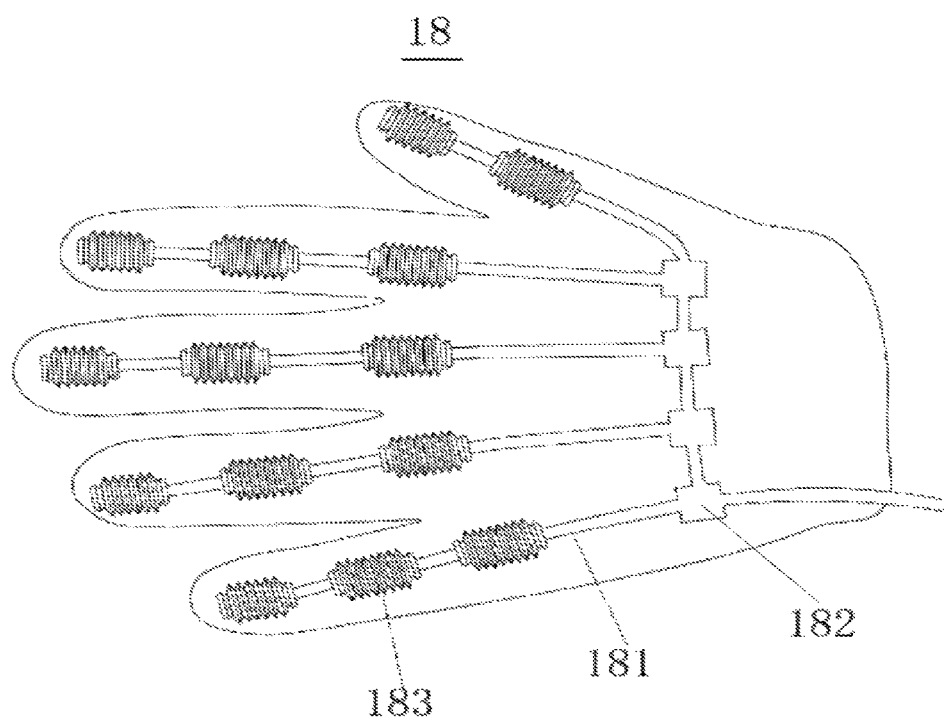
FIG. 3 is a structural diagram of a wearable training member of the present disclosure.

FIG. 3 is a structural diagram of a wearable training member of the present disclosure. In some embodiments of the present disclosure, referring to FIG. 3, the wearable training member 18 is in the shape of a glove, and specifically includes air pipes 181, three-way devices 182 and bellows 183 fixed to the glove, and the air pipes 181, the three-way devices 182 and the bellows 183 constitute a set of pneumatic components (not shown). The air pipes 181 are disposed in a direction of each finger of the glove, and the air pipe at the root of each finger is connected by four three-way devices 182 and connected to air connectors (not shown). The bellows 183 are disposed at each joint of the glove, and adjacent bellows 183 are connected through the air pipes 181. When the bellows 183 are inflated, an internal air pressure of the bellows 183 increases, lengths of the bellows 183 become larger, and the bellows 183 are in a stretched state, so that the wearable training member 18 is in a flexion condition, and each finger of the glove is bent. When the bellows 183 are pumped, the internal air pressure of the bellows 183 decreases, the lengths of the bellows 183 become smaller, and the bellows 183 are in a compressed state, so that the wearable training member 18 is in a stretching condition and each finger of the glove is straightened. When the finger joint rehabilitation training device is just started, the control member drives the gas circuit system 11 to pump air into the bellows 183 through the air pipes 181 and the three-way devices 182. The inner air pressure of the bellows 183 is reduced, the lengths of the bellows 183 are reduced, and the bellows 183 are in the compressed state, so that the wearable training member 18 is in the stretching condition, and each finger of the glove is straightened. At this time, the wearing resistance of the glove to the patient is greatly reduced, and it is convenient for the patient to wear the wearable training member.

In some embodiments of the present disclosure, the third connection port of the third three-way pipe is detachably connected to the wearable training member.

In some specific embodiments of the present disclosure, one side of the housing is provided with a wearable training member interface, the third connection port of the third three-way pipe is connected to the wearable training member interface, and the air connector is connected to the wearable training member interface through in-line, screw or buckle mode.

In some embodiments of the present disclosure, the first three-way pipe, the second three-way pipe, and the third three-way pipe are all hollow hoses. Specifically, the first three-way pipe, the second three-way pipe and the third three-way pipe are made of one of silica gel, polyethylene and polyurethane. The hose has a certain flexibility, which can prevent the first three-way pipe, the second three-way pipe and the third three-way pipe from being damaged when the first pump and the second pump work abnormally, and the silica gel, polyethylene or polyurethane material has strong aging resistance and certain elasticity, which can enhance the service life of the first three-way pipe, the second three-way pipe and the third three-way pipe.

In some embodiments of the present disclosure, the first pump and the second pump are vacuum pumps. The first positive pressure port and the second positive pressure port have a maximum positive pressure of 120 kpa to avoid excessive output pressure of the first pump and the second pump resulting in breakage of the first three-way pipe, the second three-way pipe and the third three-way pipe by excessive expansion. The first negative pressure port and the second negative pressure port have a maximum negative pressure of −65 kpa to avoid excessive pumping pressure of the first pump and the second pump resulting in breakage of the first three-way pipe, the second three-way pipe and the third three-way pipe by excessive contraction.

In some embodiments of the present disclosure, the data acquisition member includes a pressing unit and a housing, the pressing unit includes m conductive sheets, m is a natural number greater than or equal to 1, and it is convenient to acquire hand motion information of users by means of electrical signals, and m conductive sheets ensure contact sensitivity. The pressing unit is disposed in the housing, and a pressing member is disposed on an outer side of the housing, the pressing member is made of an elastic material, which is convenient for pressing the pressing unit through the pressing member, and the pressing member is disposed in parallel with the conductive sheets to save labor when pressing. The control member includes a signal detection unit, which is electrically connected to the pressing unit to facilitate detection of whether the pressing unit is pressed or not.

In some embodiments of the present disclosure, the data acquisition member includes a housing and a pressing unit disposed in the housing, the pressing unit includes at least one pressure sensitive device, the outer side of the housing is provided with a pressing member, the pressing member is made of an elastic material, the control member includes a signal detection unit, the signal detection unit is electrically connected to the pressing unit. Specifically, the signal detection unit is a voltage detection device or a current detection device. The voltage detection device or the current detection device is the known technique in the art and will not be described in detail herein.

Figure 4:
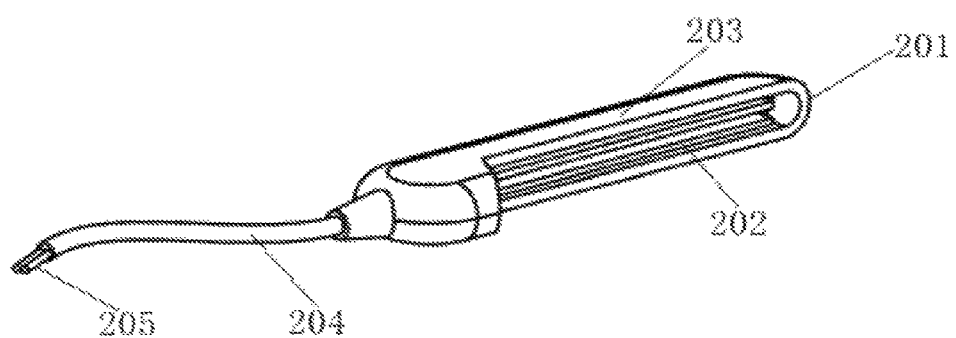
FIG. 4 is a structural diagram of a first data acquisition member of the present disclosure.

FIG. 4 is a structural diagram of a first data acquisition member of the present disclosure. In some embodiments of the present disclosure, referring to FIG. 4, the data acquisition member (not shown) includes a housing 201 and a conductive sheet group 202 disposed in the housing 201. The conductive sheet group 202 includes two conductive sheets (not shown) which are parallel to each other. One pressing member 203 is disposed on the housing 201, the pressing member 203 is parallel to the conductive sheets, and the pressing member 203 is opposite to the palm. The data acquisition member (not shown) also includes a wire group 204 for communicating the conductive sheet group 202 and the control member (not shown). The wire group 204 includes two wires (not shown), one ends of the two wires are respectively connected to two of the conductive sheets, and the other ends of the two wires are provided with a common electrical contact 205.

In some preferred embodiments of the present disclosure, the housing is made of rubber.

In some preferred embodiments of the present disclosure, a rubber sleeve is provided on an outside of the wire group for protecting the two wires.

Figure 5:
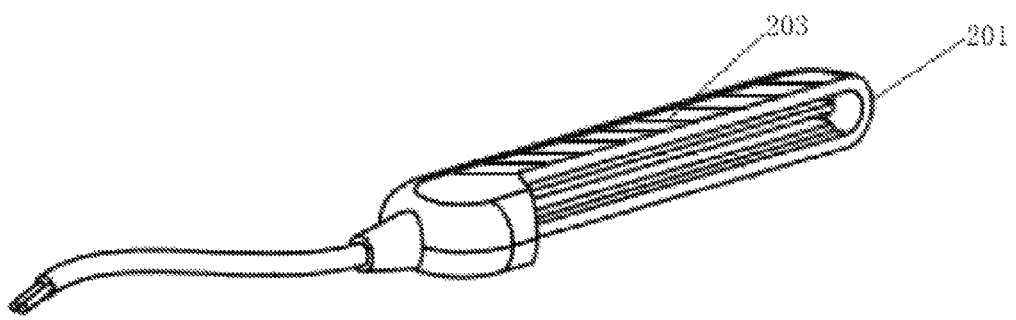
FIG. 5 is a structural diagram of a second data acquisition member of the present disclosure.

FIG. 5 is a structural diagram of a second data acquisition member of the present disclosure. In some embodiments of the present disclosure, referring to FIG. 5, FIG. 5 differs from FIG. 4 in that the housing 201 is provided with a plurality of pressing members 203, the housing 201 is provided with a plurality of mounting grooves, the pressing members 203 have a block structure and are disposed in the mounting grooves in sequence. When a plurality of the pressing members 203 are provided, the sensitivity of contact between the user and the pressing unit is improved, and it is possible to effectively prevent the failure of the data acquisition member caused by the non-response of one of the pressing members, and when one of the pressing members is damaged, the other pressing members can be used to press the pressing unit in the data acquisition member, so as to ensure that the finger pulp or fingertip can press the pressing unit when a user clenches a fist.

In some embodiments of the present disclosure, a plurality of pressing units are disposed in the housing at intervals, the pressing members are provided with a plurality of pressing members and are adapted to the pressing units, a plurality of pressing units disposed at intervals are disposed in the housing, and each pressing unit is provided with the pressing member, which improves the sensitivity of contact between the user and the pressing unit, can effectively prevent the failure of the data acquisition member caused by the non-response of a certain pressing member, and when one of the pressing units is damaged, the hand motion information of the first hand can be acquired by other pressing units to ensure the normal use of the data acquisition member.

Figure 6:
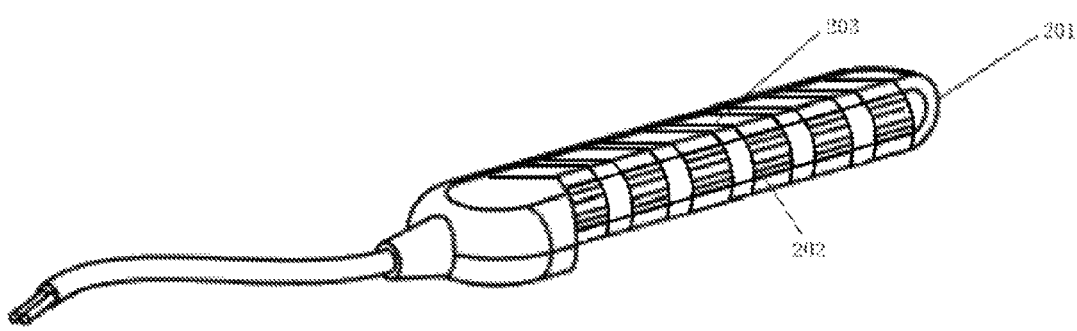
FIG. 6 is a structural diagram of a third data acquisition member of the present disclosure.

FIG. 6 is a structural diagram of a third data acquisition member of the present disclosure. In some embodiments of the present disclosure, referring to FIG. 6, FIG. 6 differs from FIG. 5 in that the housing 201 is provided with a plurality of conductive sheet groups 202, the conductive sheet groups 202 are disposed in the housing 201 at intervals, the housing 201 corresponding to each of the conductive sheet groups 202 is provided with a corresponding pressing member 203, so that each pressing member 203 independently presses and controls each of the conductive sheet groups 202, so that when one of the conductive sheet groups 202 is damaged, the hand motion information of the first hand can be acquired through other conductive sheet groups 202 to ensure the normal use of the data acquisition member.

In some embodiments of the present disclosure, a housing of the data acquisition member has a length of 0.1 to 10 cm, the number of the pressing members is 1 to 10, and the pressing members are disposed on an outer side of the housing at equal intervals, thereby ensuring the sensitivity of contact and avoiding failure to press the pressing unit during pressing.

In some embodiments of the present disclosure, the housing of the data acquisition member has a length of 2 to 6 cm, which is suitable for adults, and the number of the pressing members is 1 to 8, which ensures that users can effectively press. In some other preferred embodiments of the present disclosure, the housing of the data acquisition member has a length of 4 cm and the number of the pressing members is 5.

In other embodiments of the present disclosure, the housing of the data acquisition member has a length of 1 to 3 cm, which is suitable for children, and the number of the pressing members is 3 to 6, which ensures that the user can effectively press. In some other preferred embodiments of the present disclosure, the housing of the data acquisition member has a length of 2 cm and the number of the pressing members is 4.

In other embodiments of the present disclosure, the housing of the data acquisition member has a length of 10 cm, which is suitable for people with large palms, and the number of pressing members is 10, which ensures that users can effectively press. In some other preferred embodiments of the present disclosure, the housing of the data acquisition member has a length of 10 cm and the number of the pressing members is 2, which is convenient for fabrication.

In further embodiments of the present disclosure, the housing of the data acquisition member has a length of 0.1 cm, and the number of the pressing members is one. At this time, the data acquisition member can be disposed on a wearable data member, and the housing of the data acquisition member has a length of 0.1 cm, so that the precision of the press is made more difficult, allowing for adequate training of the hand.

Figure 7:
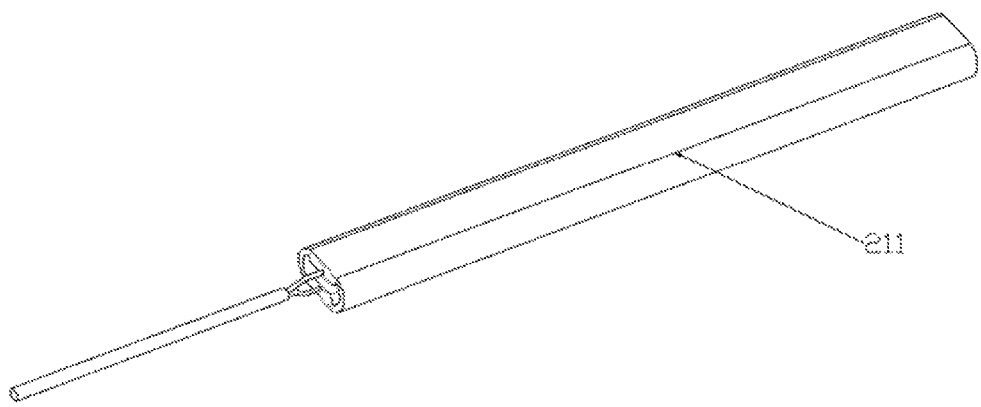
FIG. 7 is a structural diagram of a fourth data acquisition member of the present disclosure.
Figure 8:
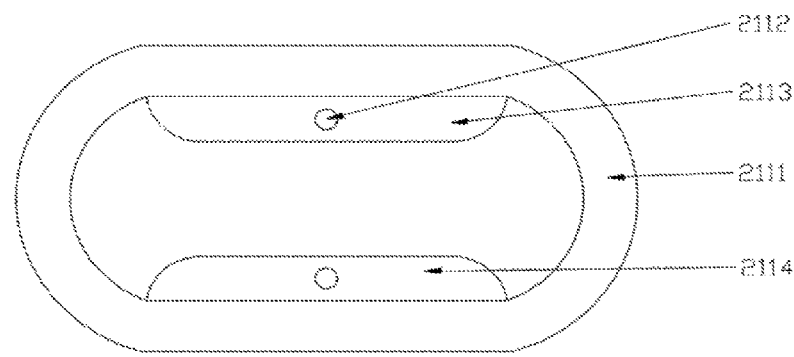
FIG. 8 is a structural diagram of a pressure sensitive element of the present disclosure.

FIG. 7 is a structural diagram of a fourth data acquisition member of the present disclosure; and FIG. 8 is a structural diagram of a pressure sensitive element of the present disclosure.

In some embodiments of the present disclosure, referring to FIGS. 7 and 8, the data acquisition member includes a pressure sensitive element 211. The pressure sensitive element 211 includes an elastic housing 2111 and a conductive adhesive layer (not shown). The conductive adhesive layer (not shown) is composed of a conductive adhesive and copper wires 2112 embedded in the conductive adhesive. The conductive adhesive layer (not shown) includes a first conductive adhesive layer 2113 and a second conductive adhesive layer 2114. The first conductive adhesive layer 2113 and the second conductive adhesive layer 2114 are not in contact with each other and are respectively disposed on opposite inner side walls of the elastic housing 2111. The data acquisition member is in a form of a pressure sensitive element, has good softness, is easier to press and acquire hand pressing information, and has a simple structure and ingenious design. The first conductive adhesive layer 2113 and the second conductive adhesive layer 2114 are not in contact with each other and are respectively disposed on the opposite inner side walls of the elastic housing 2111. When a finger presses the pressure sensitive element, the first conductive adhesive layer 2113 and the second conductive adhesive layer 2114 are in contact with each other to generate an electrical signal, thereby acquiring the hand pressing information, and any position of the pressure sensitive element is pressed, so long as the first conductive adhesive layer 2113 and the second conductive adhesive layer 2114 can contact each other to generate electrical signals, the hand pressing information can be acquired, and the pressure-sensitive element is more convenient to acquire the hand pressing information, and the feedback is more sensitive and accurate. The control member includes a signal detection unit, and the signal detection unit is electrically connected to the pressure sensitive element 211 via the copper wire 2112 to facilitate detection of an electrical signal generated by contact between the first conductive adhesive layer and the second conductive adhesive layer, and the signal detection unit is electrically connected to the copper wire to supply power to the pressure sensitive element.

Figure 9:
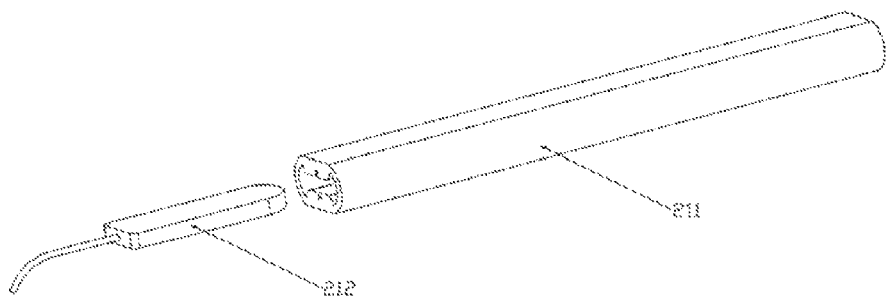
FIG. 9 is a structural diagram of a fifth data acquisition member of the present disclosure.

FIG. 9 is a structural diagram of a fifth data acquisition member of the present disclosure. In some embodiments of the present disclosure, referring to FIGS. 8 and 9, the data acquisition member includes the pressure sensitive element 211 and a conductive part 212. The pressure sensitive element 211 includes the elastic housing 2111 and the conductive adhesive layer (not shown). The conductive adhesive layer (not shown) is composed of a copper wire 2112 embedded in a conductive adhesive. The conductive adhesive layer (not shown) includes the first conductive adhesive layer 2113 and the second conductive adhesive layer 2114. The first conductive adhesive layer 2113 and the second conductive adhesive layer 2114 are not in contact with each other and are respectively disposed on the opposite inner side walls of the elastic housing 2111. The data acquisition member is in a form of a pressure sensitive element, has good softness, is easier to press and acquire hand pressing information, and has a simple structure and ingenious design. The first conductive adhesive layer 2113 and the second conductive adhesive layer 2114 are not in contact with each other and are respectively disposed on the opposite inner side walls of the elastic housing 2111. When a finger presses the pressure sensitive element, the first conductive adhesive layer 2113 and the second conductive adhesive layer 2114 are in contact with each other to generate an electrical signal, thereby acquiring the hand pressing information, and any position of the pressure sensitive element is pressed, so long as the first conductive adhesive layer 2113 and the second conductive adhesive layer 2114 can contact each other to generate electrical signals, the hand pressing information can be acquired, and the pressure-sensitive element is more convenient to acquire the hand pressing information, and the feedback is more sensitive and accurate. The conductive part 212 is provided at one end of the elastic housing 2111. Upper and lower end faces of the conductive part 212 are respectively in contact with the first conductive adhesive layer 2113 and the second conductive adhesive layer 2114. The control member includes a signal detection unit, the signal detection unit is electrically connected to the pressure sensitive element via the conductive part 212. The signal detection unit is electrically connected to the conductive part to supply power to the pressure sensitive element. The upper and lower end faces of the conductive part 212 are respectively in contact with the first conductive adhesive layer 2113 and the second conductive adhesive layer 2114, which not only increases the supporting strength at a head end of the pressure sensitive element, but also makes the electrical signal acquisition more sensitive. In certain other preferred embodiments of the present disclosure, the conductive part is a head terminal.

In some embodiments of the present disclosure, the elastic housing 2111 is made of silicone rubber.

In some embodiments of the present disclosure, the elastic housing 2111 is a long and narrow strip structure.

In some embodiments of the present disclosure, the hand motion information further includes hand light sensing information. The hand light sensing information is easier to acquire without pressing, the hand light sensing information can be detected as long as the finger flexes to block the emission of the light source, thereby driving the second hand to perform hand mirror training, the user's operation can be responded more easily and quickly, the present disclosure is suitable for people with insensitive hands, especially for people with incomplete or stiff fingers, so that a user can acquire the hand motion information by pressing or shielding the data acquisition member, and can effectively prevent the situation that the hand motion information cannot be acquired due to the inability of the user to press the data acquisition member.

In some embodiments of the present disclosure, the data acquisition member includes at least one light sensing unit, and the control member includes a signal detection unit, and the signal detection unit is electrically connected to the light sensing unit to facilitate the acquisition of the hand light sensing information. In certain other preferred embodiments of the present disclosure, the light sensing unit is a photosensitive element, such as a diffuse reflection laser sensor, an infrared sensor, etc. Structure and principle of the photosensitive element are known techniques in the art and will not be described in detail herein.

In some embodiments of the present disclosure, when the hand of the user is flexed, the hand flexing finger shields the light source emitted by the light sensing unit, and the data acquisition member acquires the hand light sensing information of the first hand where the hand is flexed to control the image (such as a character, an animal or an automobile, etc.) in the terminal equipment to move up. When the hand of the user is extended, the finger of the hand is not shielded from the light source emitted by the light sensing unit, and the data acquisition member acquires the hand light sensing information of the first hand where the hand is extended, so as to control the image (such as a character, an animal or an automobile, etc.) in the terminal equipment to move down.

In some embodiments of the present disclosure, an included angle formed by a path direction of light emitted by the light sensing unit and a direction of a finger member where the finger member is straightened is 0° to 180°. When the fingers bend or make a fist, the path of the light emitted by the light sensing unit is blocked, so as to trigger the light sensing unit to respond and convert a light signal into an electrical signal, thereby acquiring the hand light sensing information.

In some embodiments of the present disclosure, the included angle between the path direction of the light emitted by the light sensing unit and the direction of the finger member where the finger member is straightened is 0°. That is, the path direction of the light emitted by the light sensing unit is parallel to the palm corresponding location of the user and faces a metacarpophalangeal joint direction. The path of the light emitted by the light sensing unit is blocked only by slightly bending the finger of the user, thereby triggering the light sensing unit to respond and convert the light signal into the electrical signal and transmit it to the control member, to acquire the hand light sensing information, which is suitable for people with insensitive hands or people requiring low rehabilitation training intensity.

In some embodiments of the present disclosure, the included angle between the path direction of the light emitted by the light sensing unit and the direction of the finger member where the finger member is straightened is 90°. Even if the path direction of the light emitted by the light sensing unit is perpendicular to the palm corresponding location of the user, the user needs to bend fingers to be parallel to the palm corresponding location of the hand, so as to block the path of the light emitted by the light sensing unit, thereby triggering the light sensing unit to respond and convert the light signal into an electrical signal and transmit it to the control member, to acquire the hand light sensing information, so that the finger joints can be fully exercised.

In some embodiments of the present disclosure, the included angle between the path direction of the light emitted by the light sensing unit and the direction of the finger member where the finger member is straightened is 180°. Even if the path direction of the light emitted by the light sensing unit is opposite to the direction of the finger member when the finger member of the user is straightened, the user needs the finger to bend to contact with the palm corresponding location, so as to block the path of the light emitted by the light sensing unit, thereby triggering the light sensing unit to respond and convert the light signal into an electrical signal and transmit it to the control member, to acquire the hand light sensing information, so that the finger joints can be further fully exercised.

In some embodiments of the present disclosure, a plurality of light sensing units are provided, and the included angles formed by the path directions of the light emitted by the light sensing units and the direction of the finger member where the finger member is straightened are set to be the same, which improves the accuracy of acquisition of hand motion information of the first hand.

In yet another embodiment of the present disclosure, a plurality of light sensing units are provided, and the included angles formed by the path directions of the light emitted by the light sensing units and the direction of the finger member where the finger member is straightened are the same, and the path directions of the light emitted by the light sensing units are different, that is, the path directions of the light emitted by the light sensing units can be set to face different fingers, so as to facilitate the single-finger training.

In some other embodiments of the present disclosure, a plurality of light sensing units are provided, and the included angles formed by the path directions of the light emitted by the light sensing units and the direction of the finger member where the finger member is straightened are different, to ensure that the path of the light emitted by the light sensing unit can be blocked by the user's fingers bent to different angles. In some embodiments of the present disclosure, a plurality of light sensing units are provided, and the included angles formed by the path directions of the light emitted by the light sensing units and the direction of the finger member where the finger member is straightened are set to be 0°, 30°, 60°, 90°, 120°, 150° and 180°, respectively, so that the path of the light emitted by the corresponding light sensing unit can be blocked by the user's fingers bent to different angles. By analyzing the path direction of the light emitted by the light sensing unit triggering the response, a bending angle of the user's finger can be analyzed and determined, so that the movement information of the first hand can be accurately acquired, thereby contributing to determining the training intensity or rehabilitation state of the user.

In other embodiments of the present disclosure, the data acquisition member includes a pressing unit, which is pressed by a finger pulp or fingertip of a user's finger to acquire hand motion information.

In other embodiments of the present disclosure, the data acquisition member includes a light sensing unit, and the finger pulp or fingertip of a user's finger blocks the path of the light emitted by the light sensing unit to acquire hand motion information.

In other embodiments of the present disclosure, the data acquisition member includes a pressing unit and a light sensing unit, and acquires hand motion information by pressing or shielding the data acquisition member by the finger pulp or fingertip of each finger of the user. The data acquisition member includes the pressing unit and the light sensing unit, so that the acquisition of hand motion information is more accurate.

In some embodiments of the present disclosure, the finger joint rehabilitation training device further includes a wearable data member, the wearable data member is in a shape of a glove, and the data acquisition member is disposed at a palm corresponding location of the wearable data member. The data acquisition member is disposed on the wearable data member, which can effectively prevent the data acquisition member from falling off the hand of the user, is convenient for the user to use the data acquisition member, and is especially suitable for people with insensitive hands; and the data acquisition member is disposed at the palm corresponding location of the wearable data member, which is convenient for the user to press the data acquisition member.

In some specific embodiments of the present disclosure, a left-hand glove-shaped wearable data member and a right-hand glove-shaped wearable training member form a group, and a right-hand glove-shaped wearable data member and a left-hand glove-shaped wearable training member form a group. When in use, the wearable data member and the wearable training member are selected to be connected to the finger joint rehabilitation training device according to the needs of patients.

In some embodiments of the present disclosure, the palm corresponding location is provided with an accommodating part, the data acquisition member is disposed in the accommodating part, and the data acquisition member is detachably connected to the accommodating part, which is convenient for disassembling the data acquisition member and cleaning the wearable data member.

In some embodiments of the present disclosure, the accommodating part is of a mounting bag structure, and the mounting bag is provided with an opening for inserting the data acquisition device into the mounting bag.

In some embodiments of the present disclosure, the mounting bag is provided with at least one opening, the data acquisition member is provided with at least one light sensing unit, and the path of the light emitted by the light sensing unit is emitted through the opening, and the number of openings set on the mounting bag is adapted to the number of the set light sensing units.

In some better embodiments of the present disclosure, the mounting bag is of a hollow structure, so that the path of the light emitted by the light sensing unit is emitted out of the mounting bag to accurately acquire the movement information of the first hand.

In some embodiments of the present disclosure, the wearable data member further includes a suture thread for sewing and fixing an edge of the mounting bag to the palm corresponding location of the wearable data member, and sewing and fixing the mounting bag to the palm corresponding location of the wearable data member by the suture thread is convenient, simple, firm and durable, and low in cost.

Figure 10:
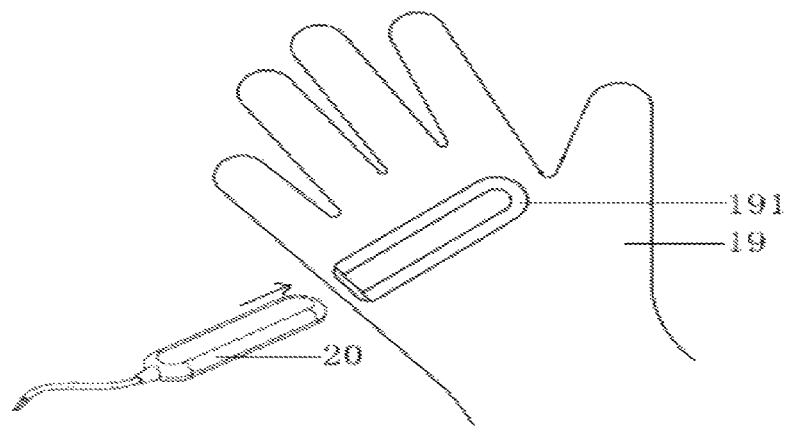
FIG. 10 is a diagram I of the data acquisition unit disposed on a wearable data member of the present disclosure.

FIG. 10 is a diagram I of the data acquisition unit disposed on a wearable data member of the present disclosure. Referring to FIG. 10, the finger joint rehabilitation training device in some embodiments of the present disclosure further includes a wearable data member 19. A palm corresponding location of the wearable data member is provided with an accommodation part 191. The accommodating part 191 is a long and narrow accommodation member, and the data acquisition member 20 is long and narrow and is adapted to the accommodating part 191. The long and narrow accommodating part is convenient for loading the data acquisition member 20, and the data acquisition member 20 is of a long and narrow structure, which ensures that the finger pulp or fingertip of each finger can be pressed to the data acquisition member when the user clenches a fist, thereby avoiding the situation that the data acquisition member cannot be used because the finger pulp or fingertip of some fingers of the user cannot be pressed to or shield the data acquisition member under special circumstances (such as finger injury, or holding something, etc.) or some special people (people with unsound five fingers). The data acquisition member 20 and the accommodating part 191 can be detachably connected to facilitate cleaning of the wearable data member 19 after disassembly.

Figure 11:
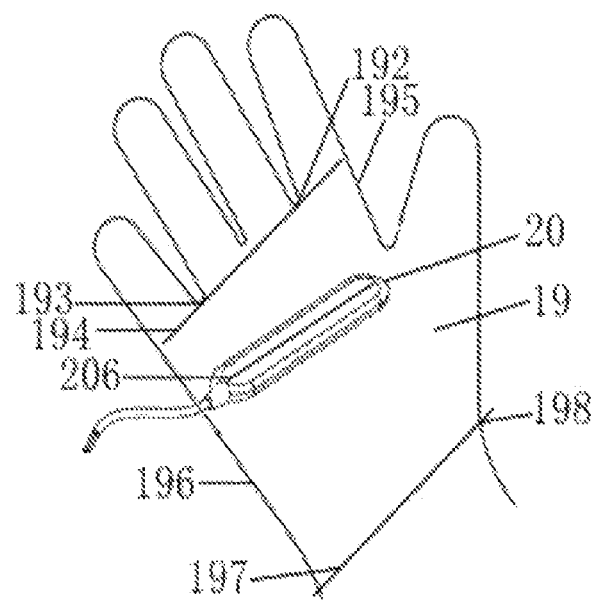
FIG. 11 is a diagram II of the data acquisition unit disposed on the wearable data member of the present disclosure.

FIG. 10 is a diagram I of the data acquisition unit disposed on a wearable data member of the present disclosure. Referring to FIG. 11, In some embodiments of the present disclosure, the data acquisition member 20 is fixed to the palm corresponding location of the wearable data member 19 by any one of pasting, hook and loop, magnetic attraction, sewing and buckling, so that the finger pulp or fingertip of each finger can be pressed to or shield the data acquisition member when a user clenches a fist, and the fixing method is simple and convenient, and the cost is low.

Referring to FIG. 11, a connection point between the middle finger and the index finger in the wearable data member 19 in the embodiment of the present disclosure is a first contact point 192, a connection point between the little finger and the ring finger is a second contact point 193, a connection point between the thumb and wrist is a third contact point 198. A straight line connecting the first contact point 192 and the second contact point 193 is a metacarpophalangeal joint line 194. A straight line passing through the third contact point 198 and parallel to the first line 194 is a palm root line 197. An edge on a little finger side of the palm corresponding location of the wearable data member 19 is an inner palm edge line 196. An edge on a thumb side of the palm corresponding location of the wearable data member 19 is an outer palm edge line 195. A line segment dividing the data acquisition member 20 (planar or three-dimensional) into symmetrical members is a first axis 206. Two ends of the first axis 206 are two symmetrical ends of the data acquisition member 20. A maximum linear distance between the inner palm edge line 196 and the outer palm edge line 195 is an axial length of the palm. A maximum linear distance between the metacarpophalangeal joint line 194 and the palm root line 197 is a radial width of the palm.

In some embodiments of the present disclosure, referring to FIG. 11, an included angle between the first axis 206 of the data acquisition member 20 and the inner palm side edge line 196 of the palm is greater than 0° and less than 180°. The data acquisition member 20 is fixed to the wearable data member 19, or disposed in the accommodating part 191 of the wearable data member 19, both of which should meet this angle setting. Because an included angle between a contact point between the finger pulp or fingertip and the palm and the inner palm edge line is different when different users clench fists, an angle of the data acquisition member in the palm corresponding location is set according to an actual contact position of the finger pulp or the fingertip and the palm when the user clenches a fist, so that the finger pulp or the fingertip can be easily pressed to or shield the data acquisition member when the user clenches a fist.

In some embodiments of the present disclosure, the angle between the first axis 206 of the data acquisition member 20 and the inner palm side edge line 196 of the palm is greater than 30° and less than 135°.

In some embodiments of the present disclosure, the included angles between the first axis 206 of the data acquisition member 20 and the inner palm side edge line 196 of the palm are 15°, 30°, 45°, 60°, 90°, 120°, 135° and 150°.

In some embodiments of the present disclosure, referring to FIG. 11, the minimum linear distance between the first axis 206 of the data acquisition member 20 and the palm root line 197 of the palm is not less than 1 cm, and the minimum linear distance between the first axis 206 of the data acquisition member 20 and the metacarpophalangeal joint line 194 of the palm is not less than 0.5 cm. The data acquisition member 20 is fixed to the wearable data member 19, or disposed in the accommodating part 191 of the wearable data member 19, both of which should meet this distance range setting. If the data acquisition member 20 is set beyond this range, the finger pulp or fingertip cannot be pressed to or shield the data acquisition member, a position of the data acquisition member 20 is matched with a position where the finger pulp or fingertip is pressed on the palm when the user clenches the fist, which ensures that the finger pulp or fingertip of the user can be pressed to or shield the data acquisition member, and facilitates acquisition of the effective hand motion information of the first hand. When the first axis 206 of the data acquisition member 20 is parallel to the palm root line 197 (or the metacarpophalangeal joint line 194), the minimum linear distance between the first axis 206 of the data acquisition member 20 and the palm root line 197 (or the metacarpophalangeal joint line 194) is the distance between two parallel lines. When the first axis 206 of the data acquisition member 20 is not parallel to the palm root line 197 (or the metacarpophalangeal joint line 194), the minimum linear distance between the first axis 206 of the data acquisition member 20 and the palm root line 197 (or the metacarpophalangeal joint line 194) is a distance from a point closest to the palm root line 197 (or the metacarpophalangeal joint line 194) on the first axis 206 of the data acquisition member 20 to the palm root line 197 (or the metacarpophalangeal joint line 194).

In some embodiments of the present disclosure, the radial width of the palm is 6 cm, and the minimum linear distance between the first axis 206 of the data acquisition member 20 and the palm root line 197 of the palm is 2 to 5 cm, and further may be 2 cm, 3 cm, 3.5 cm, 4 cm, 4.5 cm or 5 cm, etc.

In some embodiments of the present disclosure, referring to FIG. 11, a length of the first axis 206 of the data acquisition member 20 is 10% to 100% of the axial length of the palm. The data acquisition member 20 is fixed to the wearable data member 19 or disposed in the accommodating part 191 of the wearable data member 19, both of which should meet this length setting, so as to ensure that the finger pulp or fingertip of the user can be pressed to or shield the data acquisition member, which is convenient for acquiring effective hand motion information of the first hand. A size of the data acquisition member 20 is set according to a size of the palm corresponding location of the wearable data member 19, and the size of the data acquisition member 20 being relatively small can save the material input cost of the data acquisition member 20, and is suitable for users with sound and flexible hand fingers, and the size of the data acquisition member 20 being relatively large can ensure that the finger pulp or fingertip of either finger can be pressed to the data acquisition member when the user clenches a fist, and is suitable for users with inflexible hand fingers.

In some embodiments of the present disclosure, a distance between the inner palm edge line 196 and the outer palm edge line 195 is 4.5 cm, and the length of the first axis 206 of the data acquisition member 20 is 0.45 cm, 1 cm, 2 cm, 3 cm, 3.5 cm, 4 cm, 4.5 cm, etc.

In some embodiments of the present disclosure, the data acquisition member is any one of a spherical structure, an ellipsoidal structure and a polyhedral structure, which is diverse and beautiful.

In some embodiments of the present disclosure, a thickness of the data acquisition member is 0.1 to 2 cm, the thickness of the data acquisition member is small so that the training intensity can be adjusted. On the one hand, the data acquisition member is placed in the palm of the hand, and the user can press the finger pulp or fingertip of each finger to the palm of the hand by clenching the fist, and a flexion angle of the finger joints is larger when clenching the fist, which increases the training intensity of the finger joints and can fully train the finger joint. On the other hand, the user can press the data acquisition member through cooperation of the thumb and other fingers, so that the flexion angle of the finger joints is small, the training intensity is small, to ensure an appropriate training intensity, and avoid the injury to the hand due to the training intensity exceeding the hand load.

In some embodiments of the present disclosure, the data acquisition member has a flat structure, and the thickness of the data acquisition member is 0.1 to 2 cm. Specifically, the housing of the data acquisition member has a polyhedral structure, such as a rectangular parallelepiped structure. Referring to FIGS. 4, 5, and 6, for example, if the housing of the data acquisition member has a structure similar to a rectangular parallelepiped, the thickness of the data acquisition member is 0.1 to 2 cm as the thickness of the housing 201.

In some embodiments of the present disclosure, the housing of the data acquisition member is of a spherical structure, which is convenient for the user to directly grasp and use in the palm of the hand, and is convenient to press the data acquisition member when making a fist. The thickness of the data acquisition member, that is, a diameter of the spherical housing is 2 cm, and the size is suitable, Which is convenient for pulp or fingertip of each finger to press the data acquisition member cooperating with the palm of the hand when the hand of the user makes a fist.

In some embodiments of the present disclosure, the housing of the data acquisition member is of an ellipsoidal structure, which is convenient for the user to directly grasp and use in the palm of the hand, and is convenient to press the data acquisition member when making a fist. The thickness of the data acquisition member, that is, a length of a short axis of the ellipsoidal housing is 2 cm, and the size is suitable, Which is convenient for pulp or fingertip of each finger to press the data acquisition member cooperating with the palm of the hand when the hand of the user makes a fist.

In some embodiments of the present disclosure, at least one surface of the housing of the data acquisition member is a concave-convex surface, that is, convex points, concave-convex stripes, concave-convex patterns are formed on at least one surface of the housing of the data acquisition member to form a concave-convex surface, the concave-convex surface is easy to process and can provide a good anti-skid effect.

In some embodiments of the present disclosure, the finger joint rehabilitation training device further includes an external control interface, the external control interface is connected to the control member, the electrical contact is detachably connected to the external control interface, and the external control interface is disposed at one side of the device housing. Specifically, the electrical contact is connected to the data acquisition member through an in-line mode.

In some preferred embodiments of the present disclosure, the wearable training member is in a stretching condition at an initial state.

In some specific embodiments of the present disclosure, the user wears the wearable data member with his left hand and the wearable training member with the right hand. The user makes a flexion movement with the left hand, i.e., the left hand makes a fist, while the index finger, middle finger, ring finger and little finger of the left hand press on the pressing member, the two conductive sheets are brought into contact, the control member determines that the two conductive sheets are in contact according to the current or the voltage, then, the control member supplies power to the first pump, the second pump and the second valve, and cuts off power to the first valve, so that the wearable training member enters a flexion condition, and the wearable training member drives the right hand of the user to make the flexion movement, that is, the right hand clenches a fist.

In some specific embodiments of the present disclosure, the wearable training member enters the flexion condition from the stretching condition, where the required time is a first time. After the first time, the control member supplies power to the first pump, the second pump, the first valve and the second valve to maintain the wearable training member in the flexion condition.

In some specific embodiments of the present disclosure, the user wears the wearable data member with his left hand and the wearable training member with the right hand. The user makes a stretching movement with the left hand, i.e., the left hand extends horizontally, while the index finger, middle finger, ring finger and little finger of the left hand can loosen the pressing of the pressing member, to separate the two conductive sheets, the control member determines that the two conductive sheets are separated according to the current or the voltage, then, the control member supplies power to the first pump, the second pump and the first valve, and cuts off power to the second valve, so that the wearable training member enters a stretching condition, and the wearable training member drives the right hand of the user to make the stretching movement, that is, the right hand extends horizontally.

In some specific embodiments of the present disclosure, the wearable training member enters the stretching condition from the flexion condition, where the required time is a second time. After the second time, the control member supplies power to the first pump and the second pump, and cuts off power to the first valve and the second valve to maintain the wearable training member in the stretching condition.

In some embodiments of the present disclosure, the finger joint rehabilitation training device further includes a peripheral end, and the peripheral end is used for remotely controlling the finger joint rehabilitation training device, which is convenient for a guardian of a patient to adjust the finger joint rehabilitation training device. The peripheral end includes a mobile display member, a mobile key member, a first data interaction module and a mobile control member, and the mobile display member, the mobile key member and the first data interaction module are all disposed on the mobile control member.

In some embodiments of the present disclosure, the control member is provided with a second data interaction module used for data interaction with the first data interaction module, which is convenient for information interaction between the control member and the peripheral end. The second data interaction module and the first data interaction module are wirelessly connected, thereby reducing complex wiring. Specifically, the peripheral end is one of a mobile phone or a computer, and both the first data interaction module and the second data interaction module are Bluetooth modules, which are used for data transmission.

In yet another embodiment of the present disclosure, the first data interaction module and the second data interaction module are wired.

In some embodiments of the present disclosure, the first pump and the second pump enter an operational state. When the first valve is powered on and the second valve is powered off, the first permanent opening is communicated with the first regulating port, the first external interface is closed, the second permanent opening is communicated with the second external interface, the second regulating port is closed, a negative pressure is formed at the first negative pressure port and the second negative pressure port, and a positive pressure is formed at the first positive pressure port and the second positive pressure port, so that the air in the bellows enters the second three-way pipe along the air pipes, the third three-way pipe, the first regulating port and the first permanent opening in turn, passes through the first negative pressure port and the second negative pressure port respectively to enter the first pump and the second pump, passes through the first positive pressure port and the second positive pressure port to enter the first three-way pipe, and passes through the first three-way pipe to enter the second permanent opening, and is finally discharged from the second external interface, and the air in the bellows is extracted to make the wearable training member enter the stretching condition.

In some embodiments of the present disclosure, the first pump and the second pump enter an operational state. When the first valve is powered off and the second valve is powered, the first permanent opening is communicated with the first external interface, the first regulating port is closed, the second permanent opening is communicated with the second regulating opening, the second external interface is closed, a negative pressure is formed at the first negative pressure port and the second negative pressure port, a positive pressure is formed at the first positive pressure port and the second positive pressure port, so that outside air enters the second three-way pipe along the first external interface and the first permanent opening in turn, passes through the first negative pressure port and the second negative pressure port respectively to enter the first pump and the second pump, passes through the first positive pressure port and the second positive pressure port to enter the first three-way pipe, and passes through the second permanent opening, the second regulating port, the third three-way pipe and the air pipes in turn to enter the bellows, to be inflated into the bellows to make the wearable training member enter the flexion condition.

In some embodiments of the present disclosure, the first pump and the second pump enter an operational state. When both the first valve and the second valve are powered on, the first permanent opening is communicated with the first external interface, the second permanent opening is communicated with the second external interface, a positive pressure is formed at the first positive pressure port and the second positive pressure port, the air enters the second three-way pipe along the first three-way pipe, the second permanent opening, the second regulating opening, the third three-way pipe, the first regulating opening and the first permanent opening in turn, and then passes through the first negative pressure port and the second negative pressure port to enter the first pump and the second pump, respectively. The flow of air in the gas circuit system forms a circulation, and a total amount of air in the gas circuit system, the air pipes and the bellows is constant, so that the pressure in the bellows is constant, and the wearable training member maintains the current state.

In some embodiments of the present disclosure, the first pump and the second pump enter an operational state. When both the first valve and the second valve are powered off, the first regulating valve and the second regulating valve are closed, no air flows in the third three-way pipe, the air pipes and the bellows, the pressure remains unchanged, and the wearable training member maintains the current state.

Figure 12:
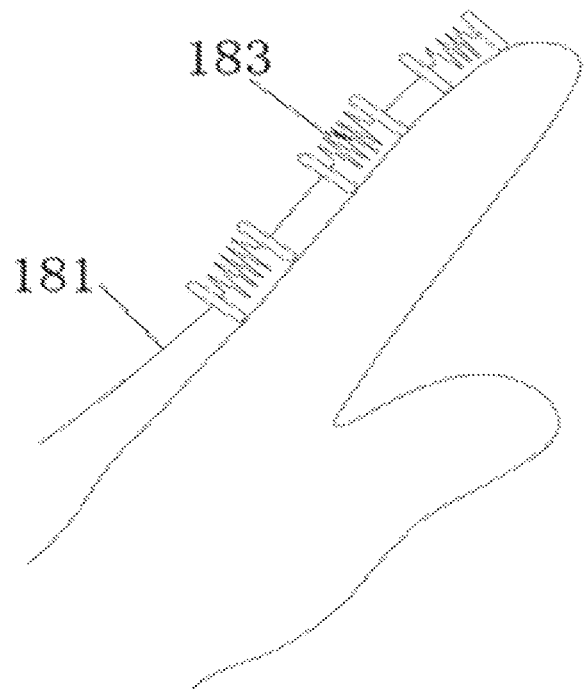
FIG. 12 is a structural diagram of the wearable training member of the present disclosure in a stretching condition.

FIG. 12 is a schematic diagram of a wearable training member in a stretching condition in some embodiments of the present disclosure. Referring to FIGS. 3 and 12, when the air in the bellows 183 is extracted through the air pipes 181, the internal air pressure of the bellows 183 decreases, the lengths of the bellows 183 become smaller, and the bellows 183 are in a compressed state, so that the wearable training member 18 is in the stretching condition, that is, each finger of the glove is straightened.

Figure 13:
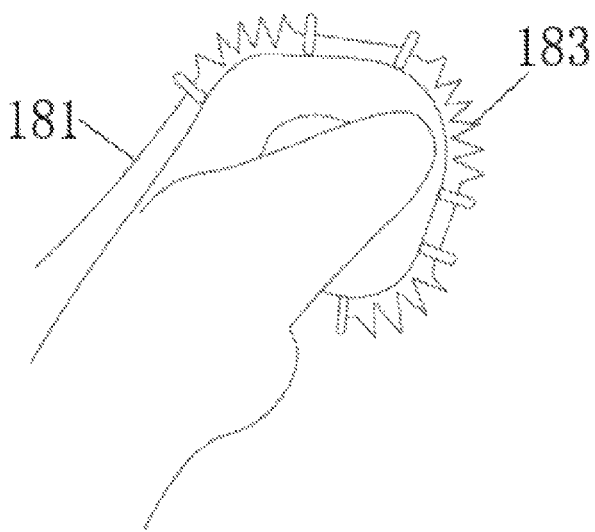
FIG. 13 is a structural diagram of the wearable training member of the present disclosure in a flexion condition.

FIG. 13 is a schematic diagram of a wearable training member in a flexion condition in some embodiments of the present disclosure. Referring to FIGS. 3 and 13, when air is inflated into the bellows 183 through the air pipes 181, an internal air pressure of the bellows 183 increases, lengths of the bellows 183 become larger, and the bellows 183 are in a stretched state, so that the wearable training member 18 is in a flexion condition, that is, each finger of the glove is bent.

In some embodiments of the present disclosure, the finger joint rehabilitation training device also includes an air pressure detection member. The air pressure detection member is respectively connected to the control member and the wearable training member. The air pressure detection member is used for detecting the air pressure in the wearable training member and transmitting the air pressure in the wearable training member to the control member. The control member is used for driving the gas circuit system to pump air to the wearable training member to a threshold air pressure of the wearable training member when starting, and is also used for calculating a grip strength of the user or performing hand training according to the air pressure detected by the air pressure detection member.

In some specific embodiments of the present disclosure, referring to FIG. 2, the air pressure detection member is disposed in the third three-way pipe 117, or a probe of the air pressure detection member is disposed in the third three-way pipe 117 to detect an air pressure value in the third three-way pipe 117.

In some embodiments of the present disclosure, referring to FIG. 2, the control member drives the gas circuit system 11 to pump air to the wearable training member to a threshold air pressure of the wearable training member, the first regulating port 1132 and the second regulating port 1142 are closed, the third three-way pipe 117 and the pneumatic component form a closed pipeline. When the hand of the patient wears the wearable training member to make a fist, that is, the wearable training member enters a flexion condition, the air pressure in the closed pipeline formed by the third three-way pipe 117 and the pneumatic component decreases, and the air pressure value in the third three-way pipe 117 is detected by the air pressure detection member, and the grip strength of the patient can be obtained through the change of the air pressure value.

In some preferred embodiments of the present disclosure, the threshold air pressure of the wearable traning member is −80 kPa to −50 kPa.

In some embodiments of the present disclosure, referring to FIG. 1, the key member 16 can also selectively perform a grip strength test, and the display screen is used for displaying the grip strength.

In some specific embodiments of the present disclosure, the air pressure detection member is an air pressure sensor, preferably a (Microelectro Mechanical Systems) MEMS sensor, and the control member is a Microcontroller Unit (MCU) or a Central Processing Unit (CPU).

In some embodiments of the present disclosure, the finger joint rehabilitation training device also includes a detection member. The detection member is used for detecting the movement information of the second hand and transmitting the movement information to the control member. The control member is used for determining a recovery state of the second hand according to the movement information of the second hand to control the gas circuit system to adjust an inflating time, a pumping time and/or an inflating amount to the pneumatic component, so as to adjust the training intensity of mirror training of the second hand. The detection member is convenient for monitoring the recovery state of the second hand in real time, so as to adjust the training intensity of the second hand in time, thereby avoiding the occurrence of hand injury caused by the training intensity exceeding the hand load, or insufficient hand training intensity caused by the situation that the ideal load is not reached, and the training effect is not achieved.

In other embodiments of the present disclosure, the finger joint rehabilitation training device further includes a storage member. The storage member is used for pre-storing a second scoring standard and is connected to the control member. The control member is used for calling the second scoring standard and comparing and analyzing the movement information of the second hand to determine the recovery state of the second hand. Based on the second scoring standard pre-stored in the storage member, the control member is convenient to call the second scoring standard and compare and analyze the movement information of the second hand to determine the recovery state of the second hand, so that the training intensity of mirror training of the second hand can be controlled and adjusted in real time.

In some embodiments of the present disclosure, the second scoring standard includes a grading standard and pre-stored hand movement information. The grade evaluation standard includes a slow recovery state grade, a medium recovery state grade, and a fast recovery state grade. The pre-stored hand movement information includes a recovery state slow movement pattern matched with the slow recovery state grade, a recovery state medium movement pattern matched with the medium recovery state grade, a recovery state fast movement pattern matched with the fast recovery state grade, so that the user can get the training feedback results in real time, which improves the enthusiasm of the user for autonomous training and has high training compliance. The movement pattern is the hand finger bending pattern, and the recovery state slow movement pattern, the recovery state medium movement pattern and the recovery state fast movement pattern are set according to different threshold ranges divided by parameters such movement bending angle, stretching time and flexion time.

In some embodiments of the present disclosure, the detection member includes a gas flow rate detection unit, the gas flow rate detection unit is connected to the control member, is used for detecting the gas flow rate in the pneumatic component. The gas flow rate in the pneumatic component is detected by the gas flow rate detection unit to obtain a bending angle of the finger member of the wearable training member, that is, the bending angle of the fingers of the second hand. The gas flow rate in the pneumatic component is large, indicating that the internal air pressure of the bellows in the pneumatic component is large, an elongation length of the bellows is large, and the stretching state is large, so that the bending angle of each finger of the wearable training member is large, which means that the hand rehabilitation state is good. The gas flow rate in the pneumatic component is small, indicating that the internal air pressure of the bellows in the pneumatic component is small, the elongation length of the bellows is small, the stretching state is small, and the bending angle of each finger of the wearable training member is small, which means that the hand rehabilitation state is poor.

In yet another embodiment of the present disclosure, the detection member includes a pressing frequency detection unit, the pressing frequency detection unit is connected to the control member, is used for detecting a switching frequency of the flexion condition and the stretching condition of the wearable training member. The pressing frequency detection unit detects the switching frequency of the flexion condition and the stretching condition of the wearable training member to obtain an action switching frequency of the wearable training member, i.e., the switching frequency of the flexion condition and the stretching condition of the second hand, which is helpful to determine the rehabilitation state of the second hand, and the switching frequency of the flexion condition and the stretching condition of the wearable training member is fast, indicating that the second hand can quickly switch between the flexion condition and the stretching condition, that is, the rehabilitation state of the hand is good. The switching frequency of the flexion condition and the stretching condition of the wearable training member is slow, which means that the second hand can not switch the flexion condition and the stretching condition quickly, which means that the hand rehabilitation state is poor.

In still other embodiments of the present disclosure, the detection unit includes a gas flow rate detection unit and a pressing frequency detection unit. The gas flow rate detection unit and the pressing frequency detection unit are respectively connected to the control member. The gas flow detection unit is used for detecting the gas flow rate in the pneumatic component. The pressing frequency detection unit is used for detecting the switching frequency of the flexion condition and the stretching condition of the wearable training member. By simultaneously monitoring the bending angle of the fingers of the second hand and the switching frequency of the flexion condition and the stretching condition of the second hand, it is more helpful to judge the rehabilitation state of the second hand.

In some embodiments of the present disclosure, a control method of a finger joint rehabilitation training device is provided, including:

S11: acquiring hand motion information of a first hand through a data acquisition member and sending the hand motion information to a control member;

S12: after receiving and analyzing the hand motion information of the first hand, the control member controlling a gas circuit system to inflate the pneumatic component or to draw air from a pneumatic component that can expand and contract; and S13: the pneumatic component inflating or pumping air to make a wearable training member change between a flexion condition and a stretching condition, so as to realize a hand mirror training of a second hand.

In further embodiments of the present disclosure, the control method of the finger joint rehabilitation training device further includes a detection step, wherein the detection step includes:

S21: detecting motion information of the second hand by a detection unit and transmitting the motion information to the control member;

S22: the control member receiving the motion information of the second hand, and calling a pre-stored second scoring standard in a storage member to compare and analyze with the motion information of the second hand to determine a recovery state of the second hand, and then controlling an inflating time, a pumping time and/or an inflating amount of the gas circuit system to the pneumatic component according to the recovery state of the second hand; and S23: the pneumatic component adjusts the inflating time, the pumping time or the inflating amount to make a wearable training member change between the flexion condition and the stretching condition, so as to adjust a training intensity of the second hand for mirror training.

While the embodiments of the present disclosure have been described in detail, it will be apparent to those skilled in the art that various modifications and variations can be made to the embodiments. However, it is to be understood that such modifications and variations are within the scope and spirit of the present disclosure as described in the appended claims. Furthermore, the present disclosure described herein is susceptible to other embodiments and may be embodied or carried out in various ways.

The invention claimed is:

1. A data acquisition device comprising a data acquisition member, wherein the data acquisition member comprises:
an elastic housing;
a first conductive adhesive layer and a copper wire embedded in the first conductive adhesive layer; and
a second conductive adhesive layer and a copper wire embedded in the second conductive adhesive layer, the first conductive adhesive layer and the second conductive adhesive layer being spaced from each other by a distance and disposed on opposite inner side walls of the elastic housing, respectively, wherein the data acquisition member is configured to be disposed on a palm of a hand such that when fingers of the hand are flexed to press the data acquisition member, the first conductive adhesive layer and the second conductive adhesive layer come into contact with each other to generate an electrical signal, such that pressing information of the hand is collected.

2. The data acquisition device according to claim 1, further comprising a wearable data member, wherein the wearable data member is provided in a glove shape, and the data acquisition member is disposed at a palm corresponding location of the wearable data member configured such that finger pulps or fingertips of the fingers are able to press the data acquisition member when the hand is wearing the wearable data member and the fingers are flexed.

3. The data acquisition device according to claim 2, wherein the palm corresponding location is provided with an accommodating part, and the data acquisition member is disposed in the accommodating part and is detachably connected to the accommodating part.

4. The data acquisition device according to claim 3, wherein the accommodating part is in a long and narrow shape, and the data acquisition member is provided in a long and narrow shape and fits with the accommodating part.

5. The data acquisition device according to claim 2, wherein the data acquisition member is fixed to the palm corresponding location in any one manner of pasting, hook and loop fastening, magnetic attraction, sewing and buckling.

6. The data acquisition device according to claim 1, wherein the electrical signal is configured to be derived from the copper wire embedded in the first conductive adhesive layer and the copper wire embedded in the second conductive adhesive layer.

7. The data acquisition device according to claim 1, wherein the data acquisition member further comprises a conductive part disposed at one end of the elastic housing, and upper and lower end faces of the conductive part are in contact with the first conductive adhesive layer and the second conductive adhesive layer, respectively, and the electrical signal is derived from the upper and lower end faces of the conductive part.

8. The data acquisition device according to claim 1, wherein a material of the elastic housing is silicone rubber.

9. The data acquisition device according to claim 1, wherein a shape of the data acquisition member is one of a sphere, an ellipsoid, or a polyhedron.

10. The data acquisition device according to claim 1, wherein at least one surface of the elastic housing of the data acquisition member is a concave-convex surface.

11. The data acquisition device according to claim 1, wherein the data acquisition member has a flat shape and has a thickness of 0.1 cm-2 cm.

12. The data acquisition device according to claim 1, wherein a minimum linear distance is configured to be between a first axis of the data acquisition member and a palm base line of the palm is not less than 1 cm, and a minimum linear distance is configured to be between the first axis of the data acquisition member and a metacarpophalangeal joint line of the palm is not less than 0.5 cm.

13. The data acquisition device according to claim 1, wherein a length of the first axis of the data acquisition member is configured to be 10% to 100% of an axial length of the palm.

14. The data acquisition device according to claim 1, wherein the included angle is configured to be between the first axis of the data acquisition member and a medial palmar margin line of the palm is greater than 0° and less than 180°.

15. A finger joint rehabilitation training device comprising a control unit;
a data acquisition device connected to the control unit and configured for acquiring hand motion information of a first hand and transmitting the hand motion information to the control unit, the hand motion information comprising hand pressing information;
a gas circuit system connected to the control unit; and
a wearable training member connected to the gas circuit system and provided with a pneumatic component that can expand and contract,
wherein the control unit is configured for controlling the gas circuit system to supply air to the pneumatic component or to draw air from the pneumatic component according to the hand motion information, such that the wearable training member performs a transition between a flexed state and an extended state to achieve a hand mirror training of a second hand, wherein the data acquisition device comprises a data acquisition member, and the data acquisition member comprises:
an elastic housing;
a first conductive adhesive layer and a copper wire embedded in the first conductive adhesive layer; and
a second conductive adhesive layer and a copper wire embedded in the second conductive adhesive layer, the first conductive adhesive layer and the second conductive adhesive layer being spaced from each other by a distance and disposed on opposite inner side walls of the elastic housing, respectively, wherein the data acquisition member is configured to be disposed on a palm of the first hand such that when fingers of the first hand are flexed to press the data acquisition member, the first conductive adhesive layer and the second conductive adhesive layer come into contact with each other to generate an electrical signal, such that pressing information of the first hand is collected.

16. The finger joint rehabilitation training device according to claim 15, wherein the data acquisition device further comprises a wearable data member, the wearable data member is provided in a glove shape, and the data acquisition member is disposed at a palm corresponding location of the wearable data member configured so that finger pulps or fingertips of the fingers are able to press the data acquisition member when the first hand is wearing the wearable data member and the fingers of the first hand are flexed.

17. The finger joint rehabilitation training device according to claim 16, wherein the palm corresponding location is provided with an accommodating part, and the data acquisition member is disposed in the accommodating part and is detachably connected to the accommodating part.

18. The finger joint rehabilitation training device according to claim 15, wherein the electrical signal is derived from the copper wire embedded in the first conductive adhesive layer and the copper wire embedded in the second conductive adhesive layer.

19. The finger joint rehabilitation training device according to claim 15, wherein the data acquisition member further comprises a conductive part disposed at one end of the elastic housing, and upper and lower end faces of the conductive part are in contact with the first conductive adhesive layer and the second conductive adhesive layer, respectively, and the electrical signal is derived from the conductive part.

20. The finger joint rehabilitation training device according to claim 15, wherein a material of the elastic housing is silicone rubber.

* * * * *